(12) United States Patent
Liu et al.

(10) Patent No.: US 11,875,695 B2
(45) Date of Patent: Jan. 16, 2024

(54) SYSTEM AND METHOD FOR PROVIDING INTELLIGENT ASSISTANCE FOR FOOD PREPARATION

(71) Applicants: GUANGDONG MIDEA KITCHEN APPLIANCES MANUFACTURING CO., LTD., Foshan (CN); MIDEA GROUP CO., LTD., Foshan (CN)

(72) Inventors: Qiang Liu, Cupertino, CA (US); Xin Yan, San Jose, CA (US)

(73) Assignees: GUANGDONG MIDEA KITCHEN APPLIANCES MANUFACTURING., CO., LTD., Foshan (CN); MIDEA GROUP CO., LTD., Foshan (CN)

( * ) Notice: Subject to any disclaimer, the term of this patent is extended or adjusted under 35 U.S.C. 154(b) by 389 days.

(21) Appl. No.: 16/570,992

(22) Filed: Sep. 13, 2019

(65) Prior Publication Data

US 2021/0082308 A1    Mar. 18, 2021

(51) Int. Cl.
G09B 19/00     (2006.01)
G06F 3/0482    (2013.01)
H04N 21/488    (2011.01)
H04N 21/442    (2011.01)
G16H 20/60     (2018.01)

(52) U.S. Cl.
CPC ......... *G09B 19/003* (2013.01); *G06F 3/0482* (2013.01); *H04N 21/44222* (2013.01); *H04N 21/4882* (2013.01); *G09B 19/0092* (2013.01); *G16H 20/60* (2018.01)

(58) Field of Classification Search
CPC . G09B 19/003; G09B 19/0092; G06F 3/0482; G06F 3/017; G06F 3/0304; G06F 3/0425; H04N 21/44222; H04N 21/4882; H04N 21/439; H04N 21/462; H04N 21/4223; H04N 21/44218; G16H 20/60; H04L 12/40013
See application file for complete search history.

(56) References Cited

U.S. PATENT DOCUMENTS

2011/0289076 A1 *  11/2011  Boyle ................... G06N 5/04
                                                707/723
2012/0300061 A1 *  11/2012  Osman ................. G06F 1/325
                                                340/436
2014/0089097 A1 *   3/2014  Byun ................ G06Q 30/0267
                                                705/14.64

(Continued)

*Primary Examiner* — Cesar B Paula
*Assistant Examiner* — John M Heffington
(74) *Attorney, Agent, or Firm* — Morgan, Lewis & Bockius LLP

(57) ABSTRACT

The method and system disclosed herein present a cooking tutorial program that provides intelligent assistance to users during meal preparation, the method and system comprise: receiving a user selection of a recipe; playing a first content item corresponding to a first preparation step of the selected recipe in a first media format; monitoring user's actions performing the first preparation step of the selected recipe; and if the user's actions performing the first preparation step meet first criteria, adjusting the playing of the first content item, including displaying the first content item in a second media format, wherein the second media format differ from the first media format in at least a size and resolution of a portion of the first content item.

8 Claims, 8 Drawing Sheets

(56) References Cited

U.S. PATENT DOCUMENTS

2016/0267716 A1\* 9/2016 Patel ...................... G09G 5/373
2017/0011649 A1\* 1/2017 Lee .................... G09B 19/0092
2022/0129068 A1\* 4/2022 Anderson .......... G02B 27/0101

\* cited by examiner

500

502 Receive a user selection of a recipe from a plurality of recipes included in an interactive recipe program, wherein recipe includes a sequence of ordered preparation steps and each preparation step corresponds to a respective sets of content items

504 In response to receiving the user selection of the recipe, play a first content item corresponding to a first preparation step of the selected recipe on a display, wherein the first content item is being played in a first media format

506 While playing the first content item, monitor user's actions performing the first preparation step of the selected recipe

508 In accordance with a determination that the user's actions performing the first preparation step meets first criteria, adjust the playing of the first content item, including displaying the first content item in a second media format, wherein the second media format differ from the first media format in at least a size and resolution of a portion of the first content item

510 While displaying the first content item, in accordance with a determination that the user's actions are indicative of a question on the first preparation step:
  search a database associated with the first preparation step to retrieve one or more corresponding answers; and
  display the retrieved one or more answers on the display concurrently with the first content item

512 While playing the first content item, control one or more cooking appliances based on a first set of control instructions associated with the first preparation step

Figure 5

SYSTEM AND METHOD FOR PROVIDING INTELLIGENT ASSISTANCE FOR FOOD PREPARATION

FIELD OF THE TECHNOLOGY

The present disclosure relates to the field of cooking appliance controls and cooking instructions, and in particular, to systems and methods for assisting users in food preparation with interactive recipe programs.

BACKGROUND OF THE TECHNOLOGY

Conventional recipes, such as video recipes, help users to prepare meals with step-by-step instructions. For example, a video recipe may guide users through a series of cooking steps (e.g., selecting ingredients, chopping vegetables, setting up cooking appliances, and so on) with video presentation and commentaries. A user can play a video recipe on a user device (e.g., smartphone) while cooking to follow the instructions.

Conventional recipes are not designed to be interactive with users. They are designed with the false assumption that all users have the same level of cooking skills. Conventional recipes are also not designed to be software applications that facilitate cooking automation.

For at least these reasons, improved systems and methods for generating and executing an interactive recipe program that provides active intelligent assistant to users for meal preparation, are highly desired.

SUMMARY

As discussed in the background, conventional recipes are not designed to be interactive with users. In some situations, when watching a video recipe, a user may have questions regarding one or more cooking steps that are not addressed by the video's commentaries. For example, the user may have a food item that is different from the one used in the video recipe (e.g., a different size, weight, freshness, place of production, and so on), and the user would like to know how the cooking steps need to be adjusted accordingly. However, since conventional recipes are designed to contain only static information, the user would have to resort to other resources (e.g., browsing an online cooking forum) for additional information. If no answer can be readily found, the user would have to improvise or resort to trials-and-errors.

In addition, conventional recipes are designed with the false assumption that all users have the same level of cooking skills. For example, an experienced user may want to skip certain parts of a video recipe as the user is already familiar with certain cooking steps. By contrast, an inexperienced user may want to repeat certain parts of the same video recipe to have a better understanding of the instructions. Conventional recipes do not provide a convenient way for users to control the playing of a video recipe during cooking.

For example, conventional recipes cannot be connected to software applications, such as grocery order and delivery applications, or hardware devices, such as Wi-Fi connected smart ovens. Users are required to carry out each step included in a conventional recipe, which is time-consuming and prone to errors.

Furthermore, conventional recipes are also not designed to be software applications that facilitate cooking automation.

Thus, improved systems and methods for an interactive recipe program that provides intelligent assistance to users for meal preparation are highly desired.

The present disclosure describes a system and method for providing intelligent assistance to users with an interactive recipe program during cooking. An interactive recipe program is a software application that guides a user through a selected meal preparation process, and interfaces with various software and hardware components in a cooking environment to facilitate the meal preparation. The interactive recipe program includes a plurality of recipes, with each recipe comprising a sequence of cooking steps, and with each cooking step illustrated by one or more content items such as a video or audio tutorial (e.g., content items are of different size, resolutions, and/or clippings, extended versions, from different shooting angles, tailored for different variations of the step, etc.). While a content item (e.g., a default content item for the current cooking step) is playing, the user can give inputs (e.g., voice inputs or gesture inputs) to change the playback of the content items (e.g., skip or repeat a particular content item). In addition, the user can submit one or more questions as inputs to the interactive recipe program while the content item is playing. For example, a question may ask how a cooking step needs to be adjusted when the ingredients used are different from the ones demonstrated in the content items. In addition, the computer system monitors the user's actions performing the current preparation step (e.g., the speed, and accuracy of the user's actions performing the current step, the degree of ease and difficulty, the amount of ingredients that the user is using, whether the user is alone or interacting with others (e.g., talking to a friend or child), etc.). In accordance with a determination that the user's actions performing the first preparation step meets first criteria (e.g., criteria indicative of the users needing various types of assistance and guidance, or adjustment of the playback format, etc.), the computer system adjusts the playing of the first content item, including displaying the first content item in a second media format, wherein the second media format differ from the first media format in at least a size and resolution of a portion of the first content item (e.g., showing a detailed zoomed view of a chef's hand in the content item). In some embodiments, in response to receiving the question, the interactive recipe program searches a database (e.g., a community-maintained question and answer database) associated with the particular cooking step to play back corresponding answers to the user. Furthermore, the interactive recipe program is designed to connect to different cooking appliances (e.g., Wi-Fi connected ovens) and software applications (e.g., grocery order and delivery mobile applications) to automate one or more parts of a selected meal preparation process. The interactive recipe program is also designed to interface with different monitoring devices in the cooking environment (e.g., cameras installed in the food preparation area) register user actions during meal preparation. For example, if the interactive recipe program determines that the detected user actions fail to fall within an acceptable action threshold, the interactive recipe program may send a warning to the user to correct a course of actions.

Based on the systems and methods described herein, various issues associated with providing cooking instructions to users can be reduced. Certain cooking steps such as preheating an oven or ordering food items online can be automated to save time and increase accuracy. A user can, while continuing to prepare meals, ask questions to an interactive recipe program regarding one or more cooking steps and receive answers in real-time. If the interactive recipe program detects that the user is performing a cooking step wrongly, the interactive recipe program can send a warning and clarification on the cooking step to the user. As a result, the described systems and methods make meal preparation, which is traditionally highly skill-based and prone to error, convenient and accessible to users with all levels of cooking skills.

In one aspect, in accordance with some embodiments, a method is performed by a computing system that is communicably coupled with a cooking appliance and that is configured to control one or more functions of the cooking appliance.

In accordance with some embodiments, a computing system includes processors and memory storing instructions that, when executed, causes the one or more processors to perform the methods described herein. In accordance with some embodiments, an electronic device includes one or more processors, and memory storing one or more programs; the one or more programs are configured to be executed by the one or more processors and the one or more programs include instructions for performing or causing performance of the operations of any of the methods described herein. In accordance with some embodiments, a non-transitory computer readable storage medium has stored therein instructions, which, when executed by an electronic device, cause the device to perform or cause the performance of the operations of any of the methods described herein. In accordance with some embodiments, an electronic device includes: means for capturing images, means for heating food items, and means for performing or causing the performance of the operations of any of the methods described herein.

Various advantages of the disclosed technical solutions are apparent in light of the descriptions below.

BRIEF DESCRIPTION OF THE DRAWINGS

The aforementioned features and advantages of the disclosed technology as well as additional features and advantages thereof will be more clearly understood hereinafter as a result of a detailed description of preferred embodiments when taken in conjunction with the drawings.

To describe the technical solutions in the embodiments of the presently disclosed technology or in the prior art more clearly, the following briefly introduces the accompanying drawings required for describing the embodiments or the prior art. Apparently, the accompanying drawings in the following description show merely some embodiments of the presently disclosed technology, and persons of ordinary skill in the art may still derive other drawings from these accompanying drawings without creative efforts.

FIG. 5 illustrates a flowchart of a method of executing an interactive recipe program in accordance with some embodiments.

Like reference numerals refer to corresponding parts throughout the several views of the drawings.

DESCRIPTION OF EMBODIMENTS

Reference will now be made in detail to embodiments, examples of which are illustrated in the accompanying drawings. In the following detailed description, numerous specific details are set forth in order to provide a thorough understanding of the subject matter presented herein. But it will be apparent to one skilled in the art that the subject matter may be practiced without these specific details. In other instances, well-known methods, procedures, components, and circuits have not been described in detail so as not to unnecessarily obscure aspects of the embodiments.

The following clearly and completely describes the technical solutions in the embodiments of the present application with reference to the accompanying drawings in the embodiments of the present application. Apparently, the described embodiments are merely a part rather than all of the embodiments of the present application. All other embodiments obtained by persons of ordinary skill in the art based on the embodiments of the present application without creative efforts shall fall within the protection scope of the present application.

Figure 1A:
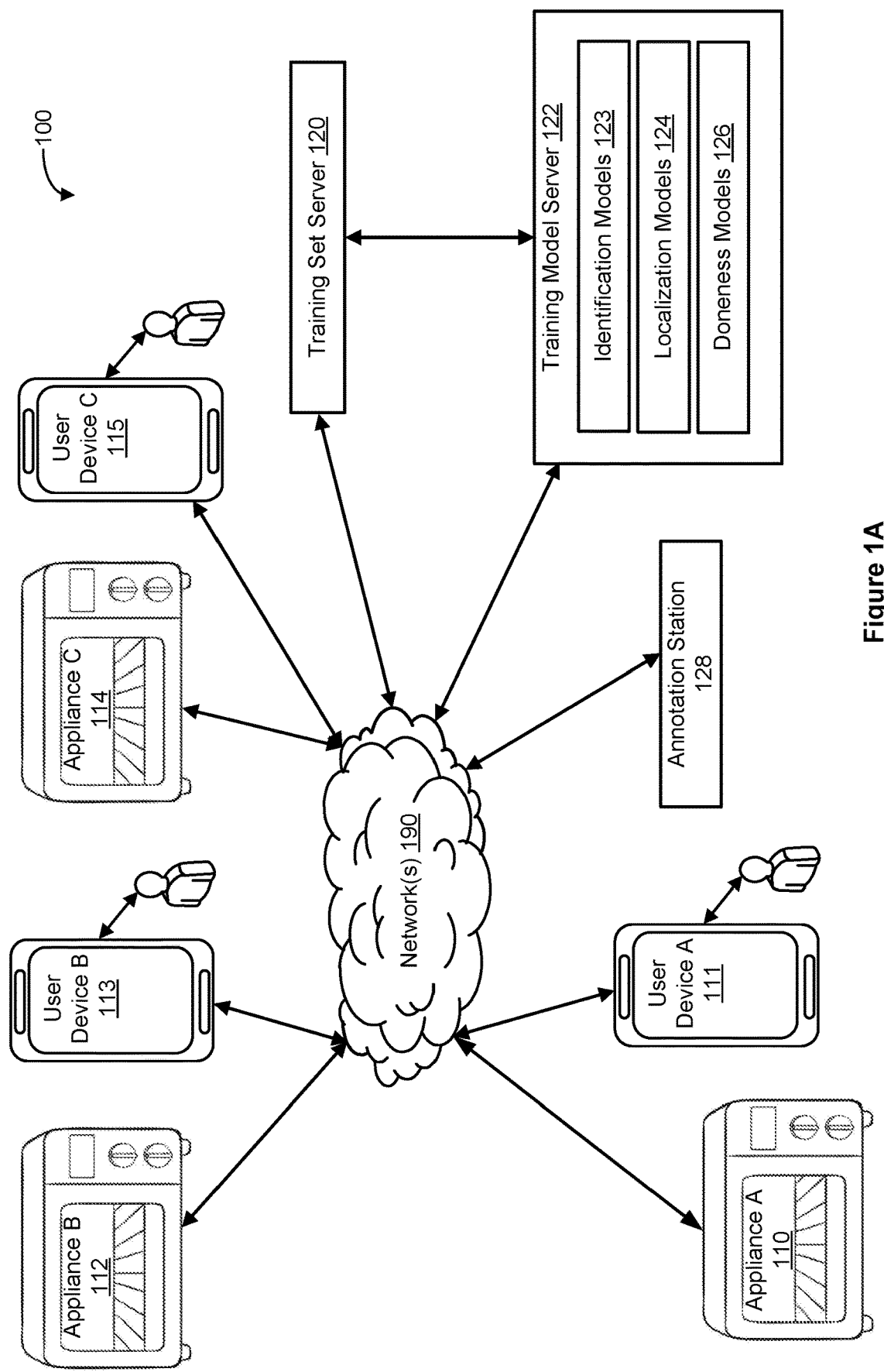
FIG. 1A shows a block diagram of an operation environment of a food preparation system (e.g., including a smart cooking appliance and related servers), in accordance with some embodiments.

FIG. 1A shows a block diagram of an operation environment 100 of a food preparation system (e.g., including a smart cooking appliance and related servers) in accordance with some embodiments.

The operation environment 100 of a food preparation system includes one or more cooking appliances (e.g., appliance A 110, appliance B 112, and appliance C 114), connected to one or more servers (e.g., training set server 120 and training model server 122), and optionally to one or more user devices (e.g., user device A 111, user device B 113, and user device C 115) and/or annotation station(s) 128, via network 190 (e.g., a wide area network such as the Internet, or a local area network such as a smart home network).

In some embodiments the one or more cooking appliances (e.g., smart ovens, smart stovetops, etc.) are configured to collect raw sensor data (e.g., image, weight, temperature, thermal map data, etc.) and send the raw sensor data to corresponding user devices (e.g., smart phones, tablet devices, etc.), annotation station 128 (e.g., workstations and desktop computers), and/or training set server 120 (e.g., server provided by the manufacturer of the cooking appliances or third-party service providers for the manufacturer). In some embodiments, the one or more cooking appliances are also configured to receive control instructions from training model server 122 and/or a corresponding user device (e.g., appliance A 110 may receive control instructions from training model server 122 to set the smart oven temperature to 425° F. for roasting vegetables and appliance A 110 may receive control instructions from user device A 111 to change the temperature to 400° F.). Additional details regarding the one or more cooking appliances (e.g., appliance A 110, appliance B 112, and appliance C 114) is described in detail with reference to other parts of the present disclosure.

In some embodiments, the one or more user devices are configured to receive raw sensor data from a respective appliance (e.g., user device A 111, which corresponds to appliance A 110, is configured to receive raw sensor data from appliance A 110). In some embodiments, the one or more user devices are also configured to send annotated data to annotation station 128 and/or training set server 120. In some embodiments, the one or more user devices are configured to generate and send control instructions to the respective appliance (e.g., user device A 111 may send instructions to appliance A 110 to turn appliance A 110 on/off or to adjust a setting on appliance A 110, such as turning on a broiler or changing the temperature of a smart oven). In some embodiments, the one or more user devices include, but is not limited to, a mobile phone, a tablet, or a computer device. In some embodiments, one or more user devices may correspond to one appliance (e.g., a computer and a mobile phone may both correspond to appliance A 110 (e.g., both are registered to be a control device for appliance A in an appliance setup process) such that appliance A 110 may send raw sensor data to either or both the computer and the mobile phone). In some embodiments, a user device corresponds to (e.g., shares data with and/or is in communication with) an appliance (e.g., user device A 111 corresponds to appliance A 110). For example, appliance A 110 may collect data (e.g., raw sensor data, such as images or temperature data) and send the collected data to user device A 111 so that the collected data may be annotated by a user on user device A 111.

In some embodiments, annotation station 128 is configured to receive collected data from the one or more appliances (e.g. appliances 110, 112, and 114) so that the collected data may be annotated by specialized annotation personnel. In some embodiments, annotation station 128 is configured to receive annotated data from the one or more user devices (e.g., user devices 111, 113, and 115) for review, editing, and/or approval by the specialized annotation personnel. In some embodiments, when annotated data from the one or more user devices have been approved at annotation station 128, annotation station sends the approved data to training set server 120 to be included in the training corpus stored at the training set server. In some embodiments, annotation station 128 retrieves annotated data from server 120 for review, editing, and/or approval by the specialized annotation personnel. In some embodiments, annotation station 128 retrieves unannotated data from server 120 for annotation by the specialized annotation personnel. Sensor data that has been annotated and/or approved at annotation station 128 is returned to server 120 for inclusion in the training corpus.

In some embodiments, training set server 120 is configured to receive raw sensor data from the one or more cooking appliances (e.g. appliances 110, 112, and 114), and/or receive annotated data from the one or more user devices (e.g., user devices 111, 113, and 115). In some embodiments, training set server 120 is also configured to send raw and/or annotated data to annotation station 128, and receive annotated and/or approved annotated data from annotation station 128. Training set server 120 is configured to preprocess the annotated data, e.g., to group, divide, and correlate the training data, and index and store the training data, in accordance with the training models and training methods employed by training model server 122. Training set server 120 is configured to send selected training data (e.g., data that includes, corresponds to, or is based on annotated data that has been approved at annotation station 128) to training model server 122, in accordance with the particular training model requesting the training data.

In some embodiments, training model server 122 is configured to receive training data from training set server 120. Training model server is also optionally configured to send control instructions (e.g., machine instructions prepared according to the control protocols of a particular cooking appliance) and/or send text data (e.g., text messages) to the one or more appliances and/or user devices. Training model server 122 includes identification models 123 (e.g., also referred to as food item identity determination model"), localization models 124 (e.g., also referred to as "food item location and outline determination model"), and doneness models 126 (e.g., also referred to as "cooking progress level determination model"). Identification models 123 are related to identifying food items being cooked in a cooking appliance. Localization models 124 are related to locating food items currently being cooked in a cooking appliance. For example, localization models 124 may be used to identify two pieces of chicken on a left side of the oven rack of the smart oven and four cookies on the right side of the oven rack of the smart oven, and outline each of them in an image captured by the smart oven. Doneness models 126 are related to determining the cooking progress level or the "done-ness" of food items present in a cooking appliance. For example, doneness models 126 may include models for determining whether a food item is fully cooked (e.g., doneness models 126 may allow a smart stovetop to determine that a piece of steak is cooked to medium-rare) or 80% cooked. Training model server 122 trains identification model 123, localization models 124 and/or doneness models 126 based on training data received from training set server 120. Once the training of identification models 123, localization models 124 and doneness models 126 are sufficiently completed (e.g., achieved a threshold level of accuracies), the training set server 120 receives requests from cooking appliances to determine food item identities and locations, and/or cooking progress levels of food items in real-time based on sensor data captured by the cooking appliances. In some embodiments, the cooking progress levels determined by the training set server 120 is provided back to the requesting cooking appliances, such that each cooking appliance determines an appropriate action, e.g., changing an operation of the cooking appliance and/or alerting a user, based on the determined cooking progress levels.

In some embodiments, cooking appliances (e.g. appliances 110, 112, and 114), user devices (e.g., user devices 111, 113, and 115), annotation station 128, training set server 120, and training model server 122 are connected (e.g., sharing data with and/or in communication with) through one or more networks 190. One or more networks 190 may include wired and wireless networks and may be a local area network of a home or a wide area network (e.g., Internet).

Figure 1B:
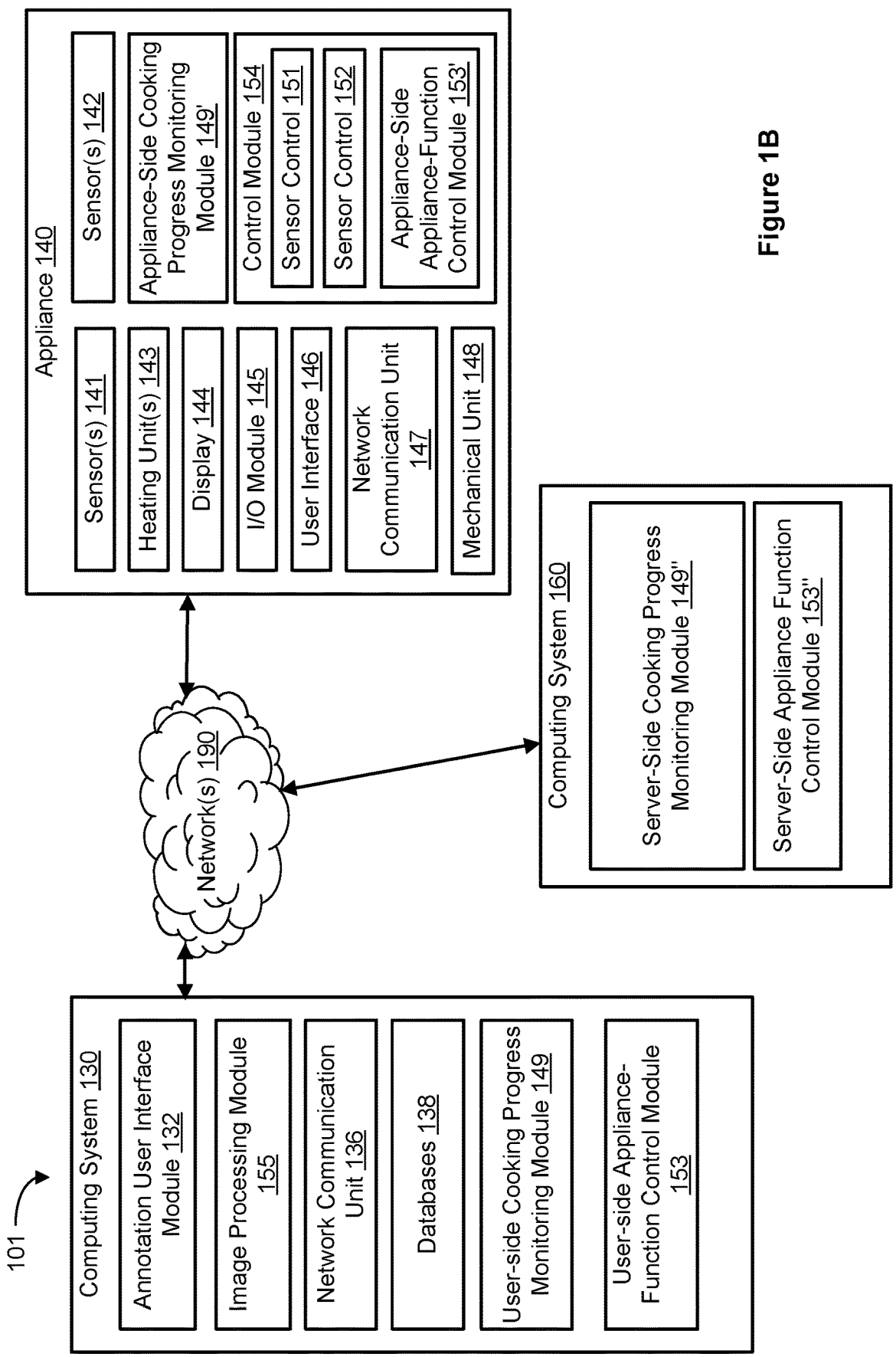
FIGS. 1B-1C show block diagrams of a food preparation system, in accordance with some embodiments.

FIG. 1B shows block diagrams of a food preparation system 101 in accordance with some embodiments.

In some embodiments, as shown in FIG. 1B, food preparation system 101 includes cooking appliance 140 and computing system 130 that is implemented separately from cooking appliance 140. Cooking appliance 140 can serve as any of cooking appliances 110, 112, and 114 in FIG. 1A. In some embodiments, computing system 130 is in communication with cooking appliance 140 through one or more networks 190. In some embodiments, computing system 130 is implemented on a user device (e.g., in association with a user application for controlling and interacting with the cooking appliance). In some embodiments, computing system 130 and appliance 140 further communicate with computing system 160 to accomplish some of the functions on computing system 130 and appliance 140 in accordance with a client-server configuration. In some embodiments, computing system 160 is implemented on a server of a manufacturer of the cooking appliance (e.g., on training model server 122). In some embodiments, computing system 160 is implemented on a standalone computer (e.g., on a local server of a smart home).

Referring to FIG. 1B, computing system 130 includes one or more of annotation user interface module 132, imaging processing module 134, network communication unit 136, and one or more databases 138. Computing system 130 corresponds to user devices as described above with respect to FIG. 1A (e.g., user devices 111, 113, and 115). In some embodiments, computing system 130 further includes user-side cooking progress monitoring module 149 and user-side appliance-function control module 153 to facilitate the cooking progress monitoring and appliance control aspects of the food preparation system, in addition to the data collection and annotation aspect of the food preparation system as described herein.

In some embodiments, annotation user interface module 132 allows a user of computing system 130 to view and annotate raw sensor data received from a corresponding appliance 140 (e.g., appliance 110, 112, or 114). For example, a user may use an application on their user device (e.g., user device 111, 113, or 115) to view images and temperature data recorded by a corresponding appliance. The user may be able to add annotations and details to the collected data, described in further detail below with respect to FIG. 3, for example.

In some embodiments, image processing module 134 obtains images captured by an imaging system of appliance 140 and processes the images for analysis. The functions of image processing module 134 and the imaging system of appliance 140 are described below with respect to FIG. 2, for example.

Network communication unit 136 allows computing system 130 to communicate with appliance 140 and/or computing system 160 over one or more networks 190.

In some embodiments, databases 138 include a database of previously captured images of food items or images from other similar food preparation systems. In some embodiments, databases 138 includes ingredient databases that allow the computing system to provide nutritional information and recipes to the user.

In some embodiments, computing system 130 includes an application that provides user-side functions, such as user-side cooking progress monitoring and appliance-function control, in conjunction with computing system 160 and appliance 140. In some embodiments, the application also provides access to a social network for the user to exchange cooking images and recipes with others using the same or similar appliances, and/or to contact the manufacturer or service providers for information and services related to the appliance 140.

In some embodiments, user-side cooking progress monitoring module 149 is configured to determine cooking progress of food items based on real-time sensor data captured by appliance 140 using food item location and outline determination models and food cooking progress level determination models that have been trained on computing system 160. In some embodiments, user-side cooking progress monitoring module 149 is configured to determine the cooking progress of food items locally using a local copy of the food item location and outline determination models and food cooking progress level determination models. In some embodiments, the user-side cooking progress monitoring module 149 sends a request to computing system 160, and receive the determination results in real-time from the computing system 160. The request includes real-time sensor data captured by appliance 140, and the results are determined using food item location and outline determination models and food cooking progress level determination models that have been trained on computing system 160.

In some embodiments, user-side appliance-function control module 153 is configured to provide a user interface for the user to directly control the appliance functions (e.g., turning the appliance on/off or setting an appliance parameter, etc.), and/or automatically generate control instructions based on the result of the cooking progress monitoring. In some embodiments, the result of the cooking progress monitoring is provided to the user-side appliance-function control module 153 from the user-side cooking progress monitoring module 149. In some embodiments, the result of the cooking progress monitoring is provided to the user-side appliance-function control module 153 from computing system 160. In some embodiments, the result of the cooking progress monitoring is provided to the user-side appliance-function control module 153 from appliance 140.

In some embodiments, appliance 140 includes one or more first sensors (e.g., sensors 141), one or more heating units 143, display 144, I/O module 145, user interface 146, network communication unit 147, mechanical unit 148, control module 155, imaging system, and, optionally, appliance-side cooking progress monitoring module 149'. Control module 155 includes an optional appliance-side appliance-function control unit 153'.

In some embodiments, the one or more first sensors 141 are configured to capture structured data, such as temperature, weight, and/or humidity. Structured data, as discussed herein, refers to quantitative or state data such as temperature, humidity, time, on/off, oven mode, etc. For example, the one or more first sensors 141 may be a temperature sensor (e.g., thermometer) or a humidity sensor, or weight sensor on the food support platform of the cooking appliance 140.

In some embodiments, the one or more heating units 143 are configured to heat at least a portion of the cooking compartment of the appliance (e.g., a heating coil configured to heat a cooking chamber). Further examples of the function of one or more heating units 143 are provided below with respect to FIG. 2, for example.

In some embodiments, appliance 140 includes a display 144 that can provide information about appliance 140 to a user (e.g., the broiler function of the smart oven is currently turned on). In some embodiments, display 144 may be integrated with I/O module 145 and user interface 146 to allow the user to input information into or read out information from appliance 140. In some embodiments, display 144 in conjunction with I/O module 145 and user interface 146 provides recommendations, alerts and nutritional information to the user and receive control instructions from the user (e.g., via hardware and/or software interfaces provided by appliance 140). In some embodiments, display 144 may be a touch screen display or a display that includes buttons. In some embodiments, display 144 may be a simple display with no touch-screen features (such as a conventional LED or LCD display) and user interface 146 may be hardware buttons or knobs that can be manually controlled. In some embodiments, user interface 146 optionally includes one or more of the following a display, a speaker, a keyboard, a touch-screen, a voice input-output interface etc.

Network communication unit 147 allows appliance 140 to communicate with computing system 130 and/or computing system 160 over one or more networks 190.

Mechanical unit 148 described herein refers to hardware and corresponding software and firmware components of appliance 140 that are configured to physically change the internal sensing (e.g., imaging), heating and/or food layout configuration of the cooking appliance 140. For example, the one or more first sensors 141 may correspond to a mechanical unit such that the one or more sensors 141 are movable to scan a respective area in a cooking compartment of appliance 140 (e.g., a motor may be configured to move a sensor across a predetermined area in order to capture data across the predetermined area). In another example, the food support platform of the cooking appliance may correspond to a mechanical unit including motors and/or robotic arms to change the relative positions of the heating elements and various parts of the food supporting platform, and/or to move food items to different parts of the food support platform or food storage compartment inside the cooking appliance. In some embodiments, the mechanical units 148 of the appliance 140 are operated in accordance with instructions from the appliance-function control unit of the food preparation system (e.g., appliance-side appliance-function control module 153', user-side appliance-function control module 153, and/or server-side appliance-function control module 153").

In some embodiments, appliance-side cooking progress monitoring module 149' is configured to monitor food that is present in a cooking compartment or cooktop of appliance 140. For example, appliance-side cooking progress monitoring module 149' may, based on raw data recorded by the one or more first sensors 141 and/or the one or more second sensors 142, determine that the food has been cooked to medium doneness. In some embodiments, appliance-side cooking progress monitoring module 149' is configured to determine cooking progress of food items based on real-time sensor data captured by first sensors 141 and imaging system using food item location and outline determination models and food cooking progress level determination models that have been trained on computing system 160. In some embodiments, appliance-side cooking progress monitoring module 149' is configured to determine the cooking progress of food items locally using a local copy of the food item location and outline determination models and food cooking progress level determination models. In some embodiments, the appliance-side cooking progress monitoring module 149' sends a request to computing system 160, and receive the determination results in real-time from the computing system 160. The request includes real-time sensor data captured by appliance 140, and the results are determined using food item location and outline determination models and food cooking progress level determination models that have been trained on computing system 160.

In some embodiments, the imaging system includes one or more second sensors 142. The one or more second sensors 142 are configured to capture unstructured data. Examples of unstructured data include RGB images and thermal or infrared images. For example, the one or more second sensors 142 may be configured to capture or record still images or videos of the food present in a cooking compartment or cooktop of appliance 140. Further examples of the function of the one or more second sensors 142 are provided below with respect to FIG. 2. In some embodiments, imaging system includes a data storage system that stores the dimensions of the food cooking compartment, and the dimensions of the reference markers within the food cooking compartment, the distances between the camera and the various reference markers within the food cooking compartment, such that images taken by the cameras can be used to accurately determine the size and shape of the food items within the images. Thus, the imaging system eliminates the problems with conventional imaging systems which require the user's special attention to place a reference marker within the images or use images without the benefit of the size and location and orientation information of the items within the images. In some embodiments, the imaging system includes an image capture triggering system. For example, in some embodiments, the image capturing is triggered when the image capture triggering system detects that there has been a change in the field of view of the camera. For example, when the oven door is opened, the lighting condition in the oven will be changed, and the image capturing will be triggered in response to the opening of the oven door. In some embodiments, the image capturing is triggered when the food item starts to appear in the field of view of the camera. In some embodiments, the image capturing is triggered when then food item is completely inserted and the oven door is closed. In some embodiments, the image capture trigger system also instructs the camera to capture and store an image of the oven rack immediately before the oven door is opened, as the compartment baseline image of the interior of the oven. In some embodiments, the image capturing is triggered manually in response to a user's input, for example, after the user has inserted the food item into the food cooking compartment. Manual trigger is easier and less complicated to implement, and allows the user to purposefully capture images that best reflect the characteristics of the food item for ingredient recognition. In some embodiments, image processing module 134 obtains the images captured by the one or more second sensors 142, and preprocesses the images to remove the background from the images based on the compartment baseline image captured before the insertion of the food item. The compartment baseline image captures the exact condition of the food support platform in the food cooking compartment of the food preparation system, and provides an excellent filter for the images containing the food item to remove the background.

In some embodiments, control module 155 includes sensor control 151, sensor control 152, and appliance-side appliance-function control module 153'. Sensor control 151 is configured to control and adjust the one or more first sensors 141. For example, sensor control 151 may send instructions for the one or more first sensors 141 to record temperature data at 1-minute intervals. Sensor control 152 is configured to control and adjust the one or more second sensors 142. For example, sensor control 152 may send instructions for the one or more second sensors 142 to be moved along a first direction and to take capture a picture when the one or more second sensors 142 are at the starting position before being moved and at the final position after being moved.

Appliance-side appliance-function control module 153' is configured to control and adjust the various functions of appliance 140. For example, appliance-side appliance-function control module 153' may send instructions to heating units 143 to activate a first heating unit of the one or more heating units, or may send instructions to mechanical unit 148 to change the relative position of the food support platform. In some embodiments, appliance-side appliance-function control module 153' generates and send control instructions to various components of the appliance 140 based on preconfigured operation protocols (e.g., to implement the normal routine functions of the appliance 140). In some embodiments, appliance-side appliance-function control module 153' generates and send control instructions to various components of the appliance 140 based on real-time cooking progress monitoring of the food items within the cooking appliance (e.g., to adjust functions of the appliance 140 automatically without user intervention based on preset reactions protocols or programs). In some embodiments, appliance-side appliance-function control module 153' generates and send control instructions to various components of the appliance 140 based on real-time user instructions received from user devices or via user interface 146 of appliance 140. In some embodiments, the result of the cooking progress monitoring is provided to the appliance-side appliance-function control module 153' from the user-side cooking progress monitoring module 149. In some embodiments, the result of the cooking progress monitoring is provided to the appliance-side appliance-function control module 153' from computing system 160. In some embodiments, the result of the cooking progress monitoring is provided to the appliance-side appliance-function control module 153' from appliance-side cooking progress monitoring module 149'.

In some embodiments, computing system 160 includes server-side cooking progress monitoring module 149" and server-side appliance-function control module 153". In some embodiments, the server-side cooking progress monitoring module 149" employs identification models 123, localization models 124 and doneness models 126 shown in FIG. 1A to determine food item identity, location, outlines, and/or cooking progress levels of food items from real-time sensor data received from cooking appliance 140 (e.g., directly or through computing system 130). In some embodiments, computing system 160 is implemented by training model server 122 in FIG. 1A.

The functions of various systems within food preparation system 101 in FIG. 1B are merely illustrative. Other configurations and divisions of the functionalities are possible. Some functions of one sub-system can be implemented on another sub-system in various embodiments.

Figure 1C:
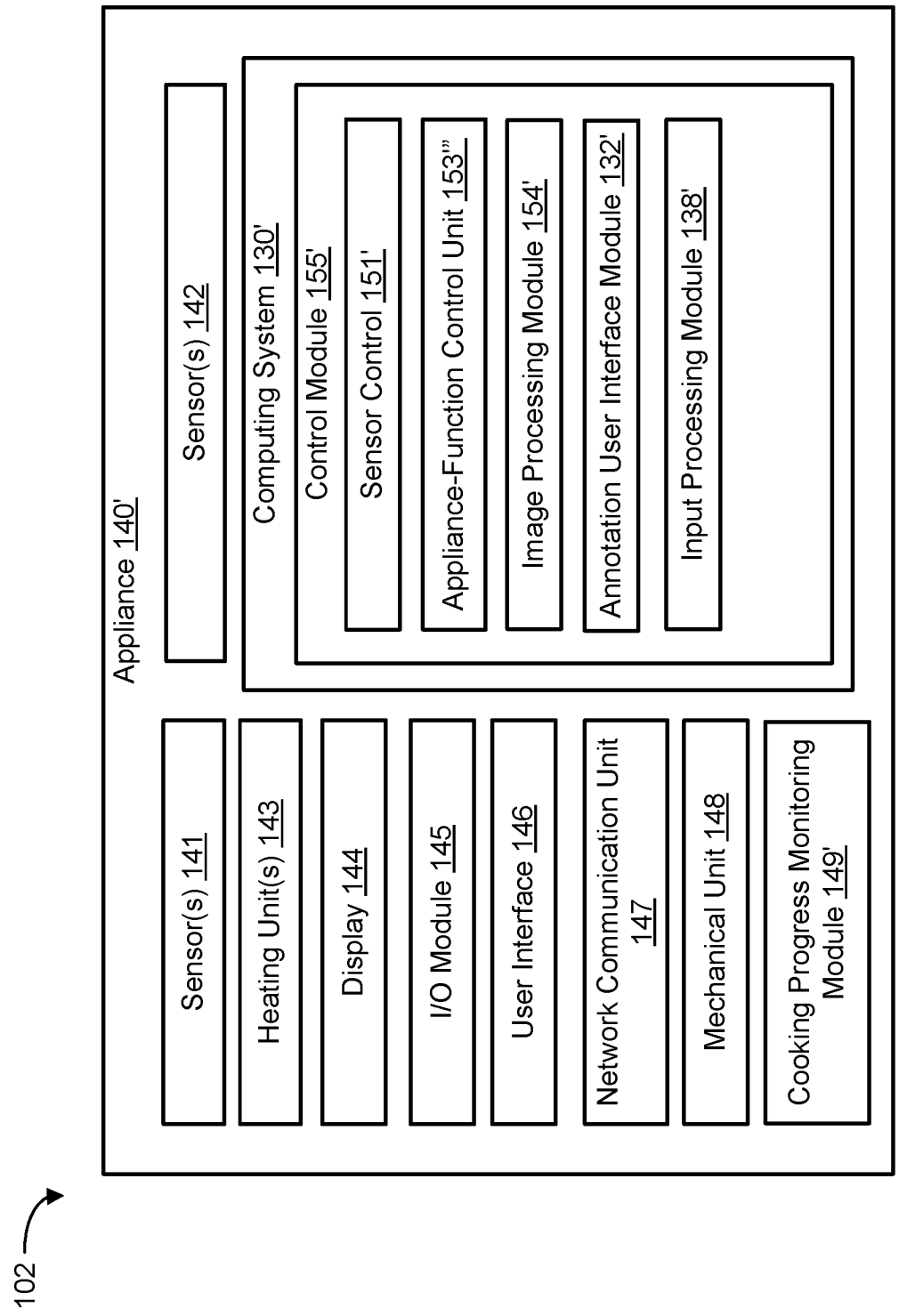

In some embodiments, as shown in FIG. 1C, food preparation system 102 includes a computing system 130' that is integrated with appliance 140'. In some embodiments, appliance 140' optionally communicates with computing system 160 to outsource some of the functions of appliance 140'.

Referring to FIG. 1C, appliance 140' has a built-in computing system 130'. Appliance 140' includes first sensors 141, second sensors 142, heating units 143, display 144, I/O module 145, user interface 146, network communication unit 147, mechanical unit 148, and imaging system. These components of appliance 140' correspond to those in appliance 140 and have similar functionalities that will not be repeated herein for brevity.

In some embodiments, computing system 130' within appliance 140' includes control unit 155', sensor control 151', sensor control 152', appliance-side cooking progress monitoring system 149''', appliance-side appliance-function control module 153''', image processing system 154', databases 138', and appliance-side annotation user interface module 132'. The functions of these components correspond to their respective counterparts with the same names in appliance 140 (e.g., sensor control 151' has the same function as sensor control 151) and will not be repeated for brevity. In some embodiments, annotation user interface module 132' may allow a user to view and annotate raw user data on a user device, separate from appliance 140'. In comparison, appliance-side annotation user interface module 132' may allow a user to view and annotate raw user data on display 144 of appliance 140' and/or annotate the cooking progress levels of food items in the images with voice input.

The above examples are provided merely for illustrative purposes. More details of the functions of the various components are set forth below with respect to other figures and illustrations. It can be understood that one or more components described herein may be used independently of other components.

Figure 2:
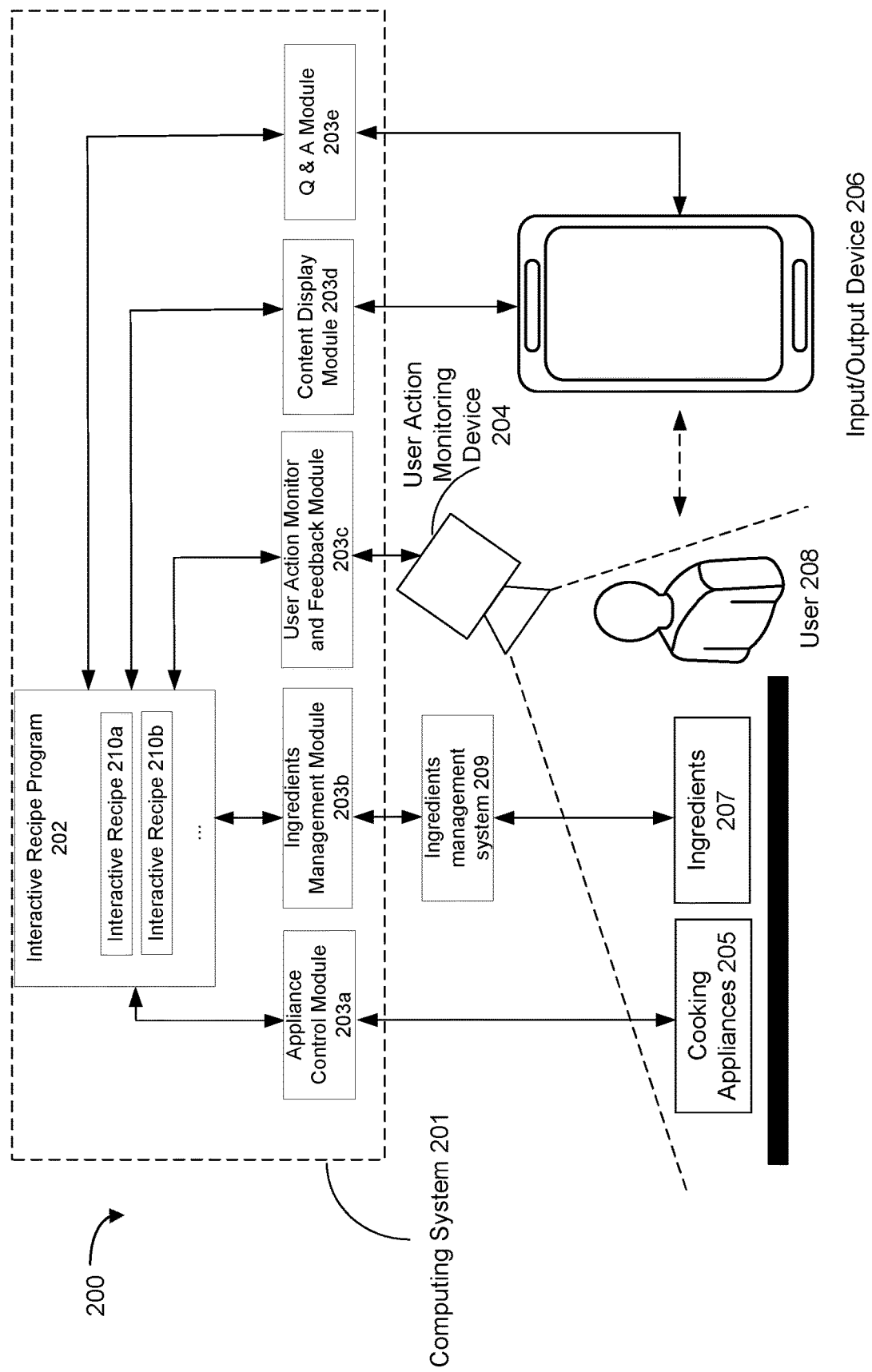
FIG. 2 is a schematic of an operation environment including a computing system running an interactive recipe program in accordance with some embodiments.
Figure 3:
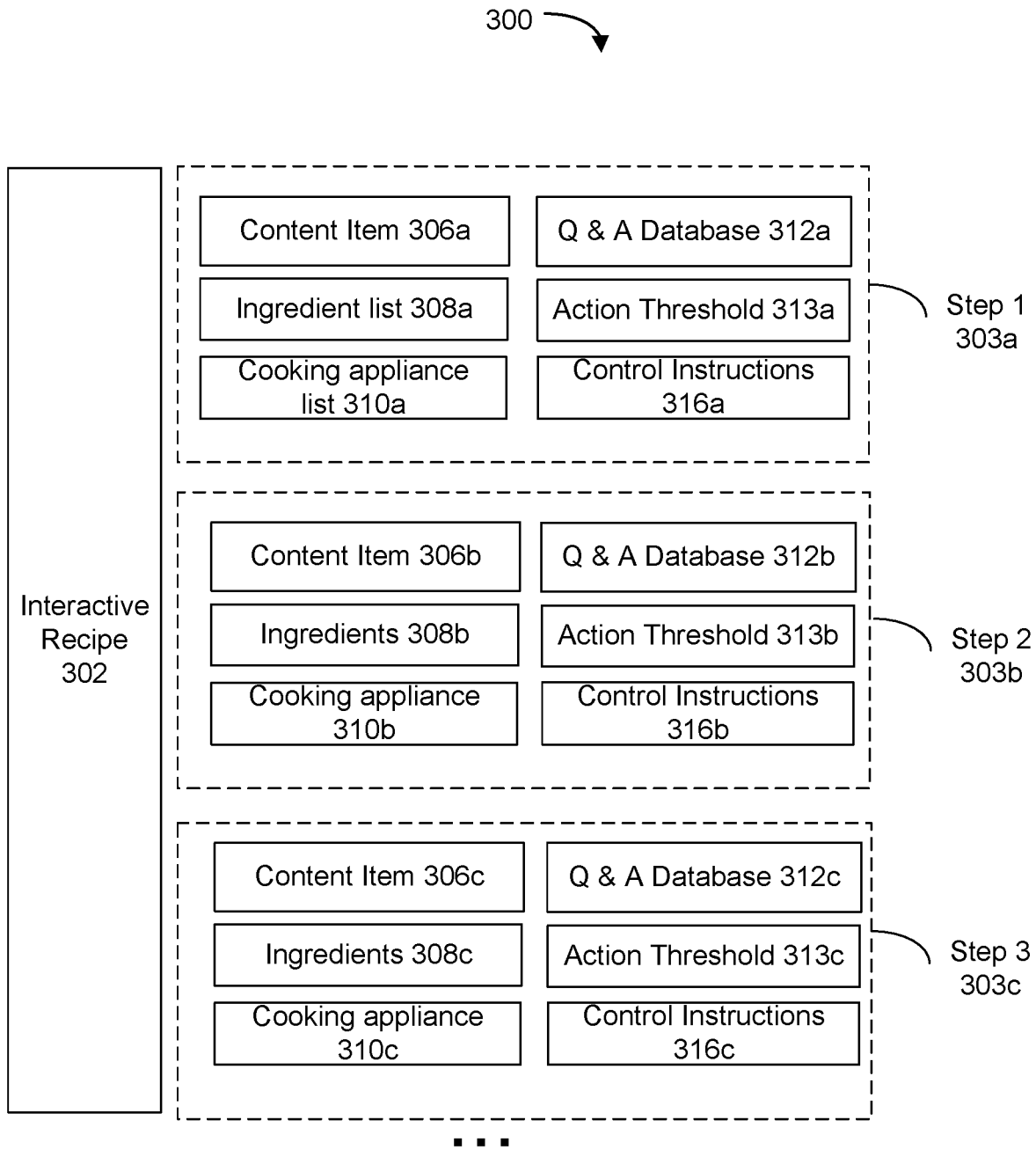
FIG. 3 is a schematic of data structure of an interactive recipe of an interactive recipe program in accordance with some embodiments.

FIG. 2 is a schematic of an exemplary operation environment 200 including computing system 201 running interactive recipe program 202 in accordance with some embodiments. In some embodiments, operation environment 200 is an environment where a user prepares meals such as a home or commercial kitchen. Operation environment 200 includes various hardware and software components, such as computing system 201, cooking appliances 205, user-action monitoring device 204, input/output device 206, ingredients management system 209, and interactive recipe program 202. In some embodiments, interactive recipe program 202 is a software program that is installed and running on computing system 201. Interactive recipe program 202 includes a plurality of prestored recipes (e.g., interactive recipes 210a-b) providing step-by-step instructions (e.g., video, audio, or text tutorials) that guide user 208 through a particular meal preparation process. Refer to FIG. 3 and the related description for exemplary data structure of an interactive recipe. In addition, interactive recipe program 202 interfaces with one or more program modules (e.g., modules 203a-203e) to communicate with various hardware and software components in operation environment 200. In some examples, the program modules are Application Programming Interfaces (APIs) for the specific hardware or software components. As a result, interactive recipe program 202 is able to control the functioning of different hardware and software components in operation environment 200.

In some embodiments, interactive recipe program 202 interfaces with one or more cooking appliances 205 via appliance control module 203a. For example, cooking appliances 205 can include ovens, stove top, range hoods, microwave ovens, and other equipment used in meal preparation. For example, interactive recipe program 202 can control cooking appliances 205 according to step-by-step cooking instructions included in a user-selected interactive recipe (e.g., interactive recipe 209a-b) such as preheating an oven, turning on/off a range hood, turning on a stove top, and so on. In some embodiments, cooking appliances 205 and computing system 201 are connected via a wireless network, such as a home Wi-Fi network.

In some embodiments, interactive recipe program 202 interfaces with an ingredients management system 209 via ingredients management module 203b. In some examples, ingredients management system 209 is designed to order new cooking ingredients online and keep track of existing ingredient inventory. For example, once user 208 selects a particular recipe in interactive recipe program 202, ingredients management module 203b checks existing inventory to determine if all the required ingredients are available. For example, ingredients management system 209 can maintain an inventory by keeping track of purchase orders (e.g., online purchase orders by an user account) and monitoring a food storage area in environment 200 with cameras and object detection algorithms. In case one or more ingredients required for a selected recipe are missing, interactive recipe program 202 prompts user 208 to order the missing ingredients from an online store.

In some embodiments, interactive recipe program 202 interfaces with one or more user action monitoring devices 204 via user action monitor and feedback module 203c. User action monitoring devices 204 include devices that collect audio, video, and other structured or unstructured data related to user actions in operation environment 200. For example, user action monitoring devices 204 can include cameras, voice recorders, motion sensors, and so on. User action monitoring devices 204 can be installed to provide full and continuous coverage of operation environment 200, such as on a ceiling of a home kitchen.

In some embodiments, each step of an interactive recipe is associated with a predefined action threshold. After detecting user actions via user action monitor and feedback module 203*b*, interactive recipe program 202 determines if the detected user action falls within the corresponding predefined action threshold. For example, the detected user action can be a stirring action (e.g., stirring dough) and interactive recipe program 202 can compare the stirring speed with a predefined speed threshold. If the detected user action does not fall within the predefined action threshold, interactive recipe program 202 provides a warning to user 208 (e.g., through the input/output device 206) and instructions on how to correct the action (e.g., stir faster).

In some embodiments, interactive recipe program 202 interfaces with input/output device 206 via content display module 203*d*. Once user 208 selects a particular recipe in interactive recipe program 202, the content items associated with the particular recipe can be played on input/out device 206. For example, the input/output device 206 can display the content items as video tutorials with commentaries. In some embodiments, the content items are divided into a sequence of ordered sub-content items, with each sub-content item corresponding to a particular step in meal preparation. In some embodiments, a next-in-line sub-content item plays only after user 208 gives an input (e.g., a voice input) to input/output device 206 to indicate continuance. In some embodiments, user 208 can select a particular format to play a sub-content item (e.g., video or audio format).

In some embodiments, interactive recipe program 202 receives a user input representing a question and generates a corresponding answer via question and answer (Q & A) module 203*e*. While playing content items for a particular recipe, user 208 may have one or more questions on a cooking step that is not addressed in the content item. In such situations, user 208 can initiate an input (e.g., voice input) to input/output device 206 representing a question; in response, Q & A module 203*e* processes the user input to generate a structured query for a database maintained by interactive recipe program 202 for the particular step. If a corresponding answer can be located for the particular query, interactive recipe program 202 uses Q & A module 203*e* to present the corresponding answer on input/output device 206.

FIG. 3 is a schematic of exemplary data structure 300 of an interactive recipe 302 in accordance with some embodiments. In some embodiments, interactive recipe 302 is one of many interactive recipes included in an interactive recipe program (e.g., interactive recipe program 202 of FIG. 2) executing on a computing system (e.g., computing system 201 of FIG. 2). Interactive recipe 302 includes step-by-step instructions for guiding a user through meal preparation. In some embodiments, interactive recipe 302 includes a sequence of ordered steps (e.g., step 1 303*a*, step 2 303*b*, step 3 303*c*, etc.), with each step directed to a particular action for a meal preparation process. An exemplary action may be chopping a food item, boiling water, stir-frying ingredients, stirring a mixture, and so on. In interactive recipe 302, each step (e.g., step 1 303*a*) is represented by data structure comprising a content item (e.g., content item 306*a*), an ingredient list (e.g., ingredients 308*a*), a cooking appliance list (e.g., cooking appliance list 310*a*), control instructions (e.g., control instructions 316*a*), an action threshold (e.g., action threshold 313*a*), and a Q & A database (e.g., Q & A database 312*a*).

The content item is a multi-media content including instructions for performing a particular action required for the selected meal preparation process (e.g., chopping vegetable). For example, the content item can be a video tutorial, an audio tutorial, and/or text that are to be displayed on a user device (e.g., input/output device 206 of FIG. 2). In the case of a video tutorial, the content item can include exemplary actions performed by a professional chef with commentaries. In some embodiments, the content item can be played in different multi-media formats (e.g., video, audio, or text). For example, a user can select the desired format, or the interactive recipe program can automatically select a format for the user. For example, if the interactive recipe program detects that the user is not looking at the input/output device for a predefined period of time while the content item is playing, the computing system can automatically switch the content item from video to audio.

In some embodiments, a user interacts with the content item such as pausing the content item, fast-forwarding in the content item, replaying the content item, playing a next content item, and so on. For example, the user can interact with the content item by giving a voice input or a touch input to the input/output device playing the content item. In some cases, when one content item (e.g., content item 306*a*) finishes playing, a following content item (e.g., content item 306*b*) automatically plays. In some other cases, for the following content item to play, the user is required to give an input to the input/output device, such as a verbal command "playing next."

While a content item is playing on the input/output device, a user may have questions or need clarification on the demonstrated cooking step. For example, the user may be using a different kind of ingredients (e.g., ingredients with different size, type, place of production, and so on) and would like to know how the demonstrated cooking step needs to be adjusted. In some embodiments, the user gives an input representing a question to the input/output device. For example, the input can be a verbal input (e.g., "how much oil is needed for searing the steak?"), or a selection from a list of most frequently asked questions displayed on the input/output device. After the input indicative of a question is submitted by the user, the interactive recipe program process the input to generate a standard query via a Q & A module. The interactive recipe program then searches a Q & A database associated with the particular cooking step using the generated query to determine if a corresponding answer exits. If a corresponding answer can be found, the interactive recipe program displays the answer on the input/output device. In some embodiments, the Q & A database is a community-maintained database and is updated as registered users upload new questions and answers.

In some embodiments, the interactive recipe program monitors user actions while a content item plays. For example, the interactive recipe program can use one or more user action monitoring devices (e.g., user action monitoring device 204 of FIG. 2) to record user actions. In another example, the interactive recipe program can use collected sensor data from cooking appliances to infer user actions. The interactive recipe program then compares the recorded user actions with corresponding action thresholds. For example, for a stirring action, the action threshold may specify the acceptable speed of stirring; for a chopping action, the action threshold may specify the size of chopped food items; for a stir-frying action, the action threshold may specify the minimum oil temperature for starting to stir-fry. If the recorded actions fail to fall within the acceptable action thresholds, the interactive recipe program can provide a warning to the user with a suggestion to correct the course of action.

The cooking appliance list in each step registers cooking appliances required for performing the respective cooking step. For example, if the cooking action associated with the step is "boiling water," a registered cooking appliance can be an electric kettle. In some embodiments, each cooking appliance is connected to a network (e.g., network 190 of FIG. 1A) with the computing system, and is identifiable by unique IP addresses in the network. If one or more required cooking appliances are not detected by the interactive recipe program, a warning is provided to the user that the corresponding step might not be properly performed.

If a required cooking appliance is detected, the interactive recipe program can send associated control instructions to the cooking appliance to automate the performance of certain cooking actions. In some embodiments, control instructions are machine code that controls one or more functions of a cooking appliance. For example, in step 1 303a, cooking appliance list 310a can include an electric oven and control instructions 316a can include instructions for heating the oven to a predefined temperature. In some embodiments, control instructions are sent to the corresponding cooking appliances only after certain preconditions are met. For example, a stove top can be turned on only after the user has placed a pot on the stove. The preconditions, e.g., the user placing a pot on the stove, can be determined via one or more user action monitoring devices (e.g., user action monitoring device 204 of FIG. 2) and user action monitor and feedback module.

The ingredient list registers the ingredients required for performing a corresponding cooking step. In some embodiments, the interactive recipe program checks with an ingredient inventory management software (e.g., ingredient management system 209 of FIG. 2) to determine if all the required ingredients are present. If one or more required ingredients for a particular step are missing, the interactive recipe program may prompt the user to order the ingredients from an online store.

Figure 4:
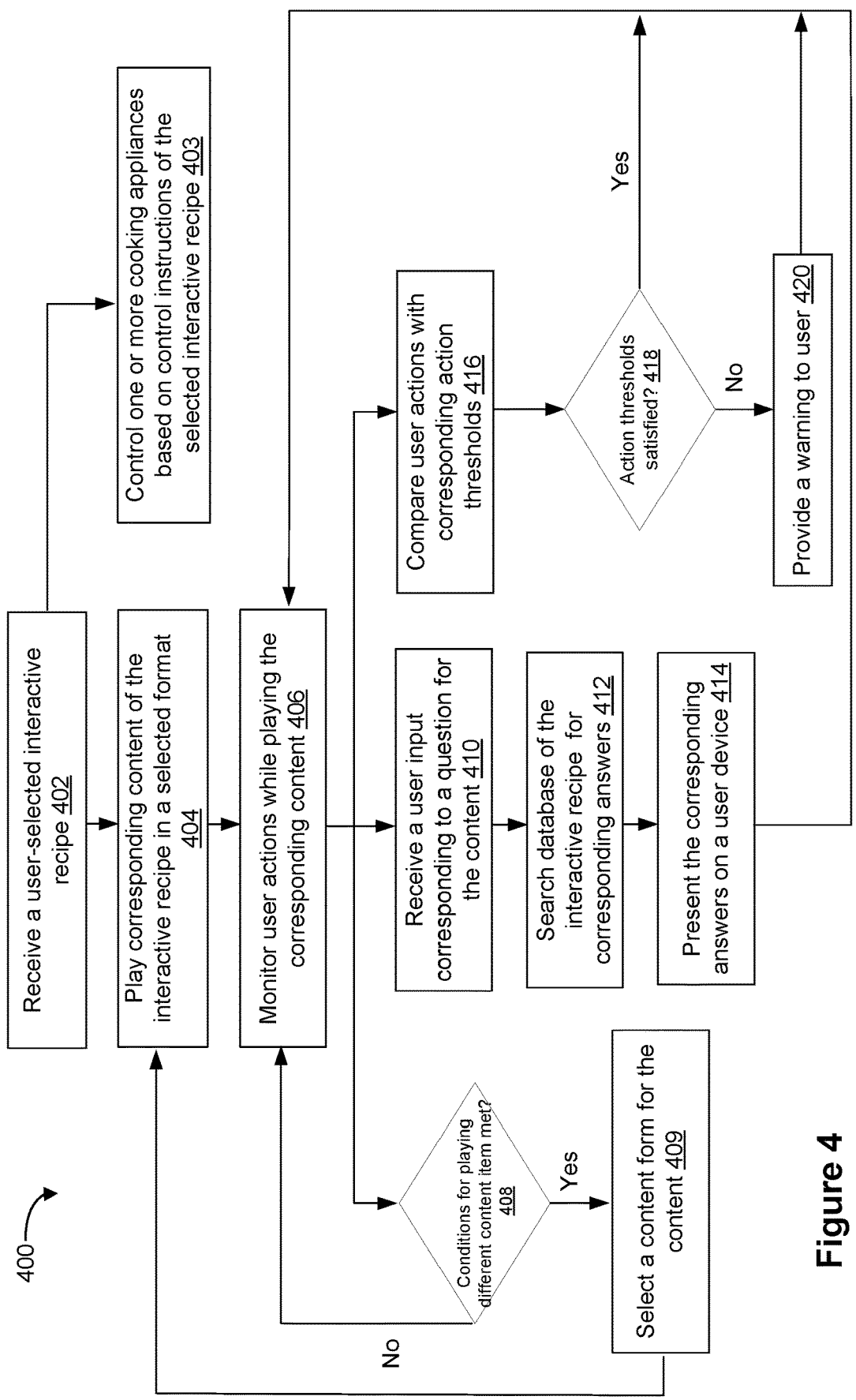
FIG. 4 illustrates an execution of an interactive recipe program in accordance with some embodiments.

FIG. 4 illustrates an exemplary execution 400 of an interactive recipe program in accordance with some embodiments. For example, the interactive recipe program can be executed on a computing system (e.g., computing system 201 of FIG. 2) that interfaces with one or more cooking appliances and user devices.

As described in FIG. 3, the interactive recipe program includes one or more interactive recipes that guide a user through different meal preparation processes. At the beginning of execution 400, a plurality of interactive recipes are displayed on an input/output device for the user to view and select. In response, the interactive recipe program receives a user-selected interactive recipe (402).

The interactive recipe program then plays a content item of the first cooking step of the selected interactive recipe (404). For example, the interactive recipe program can play the content item on an input/output device (e.g., input/output device of FIG. 2) in a user-selected format. The user has the option to specify a playing format such as video, audio, or text. Alternatively, interactive recipe program determines an appropriate format for playing the content item based on the nature of the content item and detected user actions (e.g., whether the user is looking at the input/output device).

While the content item is playing on the input/output device, the interactive recipe program concurrently controls one or more cooking appliances based on control instructions (e.g., control instructions 316a of FIG. 3) of the particular step of the selected interactive recipe (403). For example, the interactive recipe program can heat an oven to a predefined temperature, turn on/off a stove top, turn on/off a range hood, and so on. Controlling the one or more cooking appliances while the user is watching the content item increases cooking efficiency and indicates to the user the appropriate next steps.

In addition, while the content item is playing on the input/output device, the interactive recipe program monitors user actions (406). As described in FIG. 2, the interactive recipe program can use one or more monitoring devices or appliance sensors to monitor the user's actions and/or interactions with different cooking appliances.

In some embodiments, the interactive recipe program determines if conditions for playing a different content item is met (408). For example, the conditions are met when the interactive recipe program receives a user input to play the next-in-line content item. In another example, the content item associated with the following step automatically plays when the current content item finishes playing. If the conditions are met, the interactive recipe program selects an appropriate format (e.g., audio, video, or text) and plays the next content item (409, 404).

In some embodiments, while monitoring user actions, the interactive recipe program receives a user input indicative of a question (410). For example, the user input may be a verbal input related to a cooking action presented in the content item. In response, the interactive recipe program converts the user input into a structured query and searches a Q & A database associated with the content item to identify answers to the query (412). For example, a user input may be a verbal input asking "can I use soy milk to replace the required milk?" for a particular cooking step. As described in FIG. 3, the Q & A database for a particular step in the recipe can be community maintained and is updated continuously. If an answer can be found for the question, the interactive recipe program then presents the answer on the input/output device (414). For example, the interactive recipe program can pause the content item and displays the question and answer as text on the input/output device.

In some embodiments, while monitoring user actions, the interactive recipe program compares the detected user actions with corresponding action thresholds (416). If the detected user actions fall within the acceptable action thresholds (418), the interactive recipe program continues monitoring user actions. On the other hand, if the detected user actions do not fall within the acceptable action thresholds, the interactive recipe program provides a warning to the user (420) and prompts the user to correction actions.

FIG. 5 illustrates a flowchart 500 of a method of executing an interactive recipe program in accordance with some embodiments.

As the first step, the interactive recipe program receives a user-selected recipe from a plurality of recipes (502), the recipe includes a sequence of ordered preparation steps and each preparation step corresponds to a respective sets of content items. For example, the interactive recipe program can display options for different recipes on an input/output device such as a touch screen for a user to view and choose from. The input/output device can be a touch-sensitive screen that allows the user to select a recipe by contact. The recipe can be an interactive recipe that guides a user through a meal preparation process with a sequence of preparation step. In some embodiments, the recipe has data structure as described in FIG. 3, including a set of content items, a set of control instructions, a list of ingredients used for the recipe, a list of cooking appliances used for the recipe, a Q & A database, an action threshold, and so on. In some embodiments, the set of content items includes media items that focus on different aspects of the preparation step (e.g., the type of ingredient and its various types of substitutes, the chef's techniques and high resolution or slow-motion videos, videos shot from different angles, videos with different playback speeds, etc.). In some embodiments, users that have submitted their own videos for the same preparation step (e.g., with reasonable variations, such as ingredient, size, quantity variations, etc.) are also available to be viewed.

Next, the interactive recipe program plays a first content item representing a first meal preparation step of the selected recipe (504). For example, the first content item can be a video tutorial with commentaries and is displayed on the input/output device. In some embodiments, the user selects the particular format in which the first content item is played, such as video, audio, or text. In some embodiments, the first content item is a default content item in the set of content items associated with the first preparation step, and has links to various other content items in the set of content items associated with the first preparation step based on various criteria (e.g., criteria indicative of the quality of the user's execution of the first preparation step, and his/her desire for assistance and guidance).

While playing the first content item, the computer system monitors the user's actions performing the first preparation step of the selected recipe (506). For example, the cameras of the computer system monitors whether there are ambient sound or conversations, and the sound is analyzed by the computer system to determine whether the user is alone or with company. The images of the user's hands and the ambient sound are analyzed to determine the speed and ease by which the user is executing the preparation step (e.g., the speed and rhythm of the user cutting ingredients, kneading dough, stirring or beating liquids, etc.). The user's face or gaze is captured and analyzed to determine whether the user's focused on the preparation task, or is confused, or is not looking at the playback of the content item, etc.

In accordance with a determination that the user's actions performing the first preparation step meets first criteria, the computer system adjust the playing of the first content item (508), including displaying the first content item in a second media format, wherein the second media format differ from the first media format in at least a size and resolution of a portion of the first content item. In some embodiments, the first criteria include a requirement that the user's gaze is detected to be cast toward the display for more than a threshold amount of time that is greater than an average amount of time that the user typically look at the display each time the user glances at the display during performance of the current preparation step or a previous preparation step. The extended gaze is indicative of the user's interest in more details or more guidance in the preparation step. In response to the detection of the user's extended gaze, the computer optionally slows down playback of the current segment of the first content item, displays a different content item that shows more details of the preparation step (e.g., with zoomed view of the chef's hand, or slow motion playback of the chef's hand, etc.). In some embodiments, the computer displays videos provided by other users or videos shot from different angles for the first preparation step. In some embodiments, the computer system displays multiple related content items side by side in synchronized playback mode, to help the user get a full view of the chef's motion in performing the first preparation step. In some embodiments, the first criteria includes a requirement that the ambient sound of the user indicates that the user is interacting with others, e.g., in a conversation or looking at another person, or on the phone, etc. In some embodiments, the computer system mutes the sound of the currently displayed content item if the user's talking to others, and turns on closed caption after the sound it turned off. In some embodiments, the computer pauses the playback if the computer determines that the user is interacting with others. In some embodiments, the computer turns off the display and plays an audio only version of the content item, or a narration of the video (e.g., a sound recording of a narrator describing the scene in the video in addition to the techniques shown on the video, rather than just playback the sound in the video) if the user is not looking at the display and is focused on performing the task. In some embodiments, the first criteria includes a requirement that the user is performing the preparation step with at least a threshold speed and accuracy, and a requirement that the user is not looking at the display during performance of the preparation step. In some embodiments, the computer skips playback of the first content item or mute it in accordance with a determination that the user is meeting the first criteria (e.g., performing the preparation step with ease and does not need guidance). In some embodiments, the first criteria includes a requirement that the user's performance of the preparation step includes a difference from the demonstrated recipe (e.g., different ingredients, different quantity, different size, different cutting technique, etc.), and the computer searches for content item that match the variations made to the preparation step by the user and present an option to the user to playback the content items that match the variations. For example, if the recipe calls for chopped carrots, and the user is chopping yams, the computer system searches and locate other user's submissions of videos that is using the current recipe with yams replacing carrots, and offers to playback those videos for the user.

In some embodiments, while playing the first content item on the input/output device, the interactive recipe program receives user inputs, e.g., as opposed to user actions performing the preparation steps or interacting with others or the environment. For example, the interactive recipe program can receive a verbal user input or a touch input on the input/output device.

If the interactive recipe program determines that the user input is indicative of a question for the first preparation step of the selected recipe, the interactive recipe program searches a Q & A database associated with the first preparation step to retrieve corresponding answers (510). For example, the user may speak to the input/output device "Can I use soy milk instead of milk?" The corresponding answer can be displayed on the input/output device concurrently with the content item.

If the interactive recipe program determines that the user input is indicative of an adjustment to the playing of the content item, the interactive recipe program adjusts the playing accordingly. For example, the user input can be an input to pause, fast-forward, replay, or repeat certain parts of the content item, or to play the content item in a different media format.

In some embodiments, once the content item finishes playing, the interactive recipe program receives another user input indicating a request to play the next content item. In response, the interactive recipe program plays the next content item on the input/output display for the user. In some embodiments, the computer system monitors whether the user has finished performing the current preparation step, and start playing the content item associated with the next preparation step, irrespective of the playing state of the media content items associated with the previous preparation steps. In some embodiments, the computer system records the performance of the previous preparation step and uploads the video as a content item for the previous preparation step with the user's consent.

In some embodiments, the interactive recipe program controls one or more cooking appliances while the content item is playing on the input/out device (512). For example, the interactive recipe program can use the associated control instructions (e.g., control instructions 316*a* of FIG. 3) to control the cooking appliances. In another example, if a previous cooking step calls for boiling water on the stove, and while the user is performing the next step, the computer system automatically monitors the state of the stove and the water and turns off the stove or alert the user when the water boils.

In some embodiments, the interactive recipe program changes the playing format of the content item. For example, the interactive recipe program can play the content item in video, audio, or text based on user selection. In another example, the interactive recipe program can change playing format based on detected user actions. If the user is not looking at the input/out device, the interactive recipe program may change the playing format from video to audio.

In some embodiments, the interactive recipe program automatically plays a next content item without receiving a user input when one or more conditions are satisfied. For example, the interactive recipe program may automatically play the next content item in response to the current content item finishing playing, or in response to detecting the user has finished the corresponding meal preparation step of the current content item.

In some embodiments, the interactive recipe program uses one or more user action monitoring devices to monitor user actions during meal preparation. The interactive recipe program compares the detected user actions with a predefined action threshold, and if the detected user actions do not fall within acceptable action thresholds, the interactive recipe program provides a warning to the user on the input/output device with a suggestion of course of correction.

Figure 6:
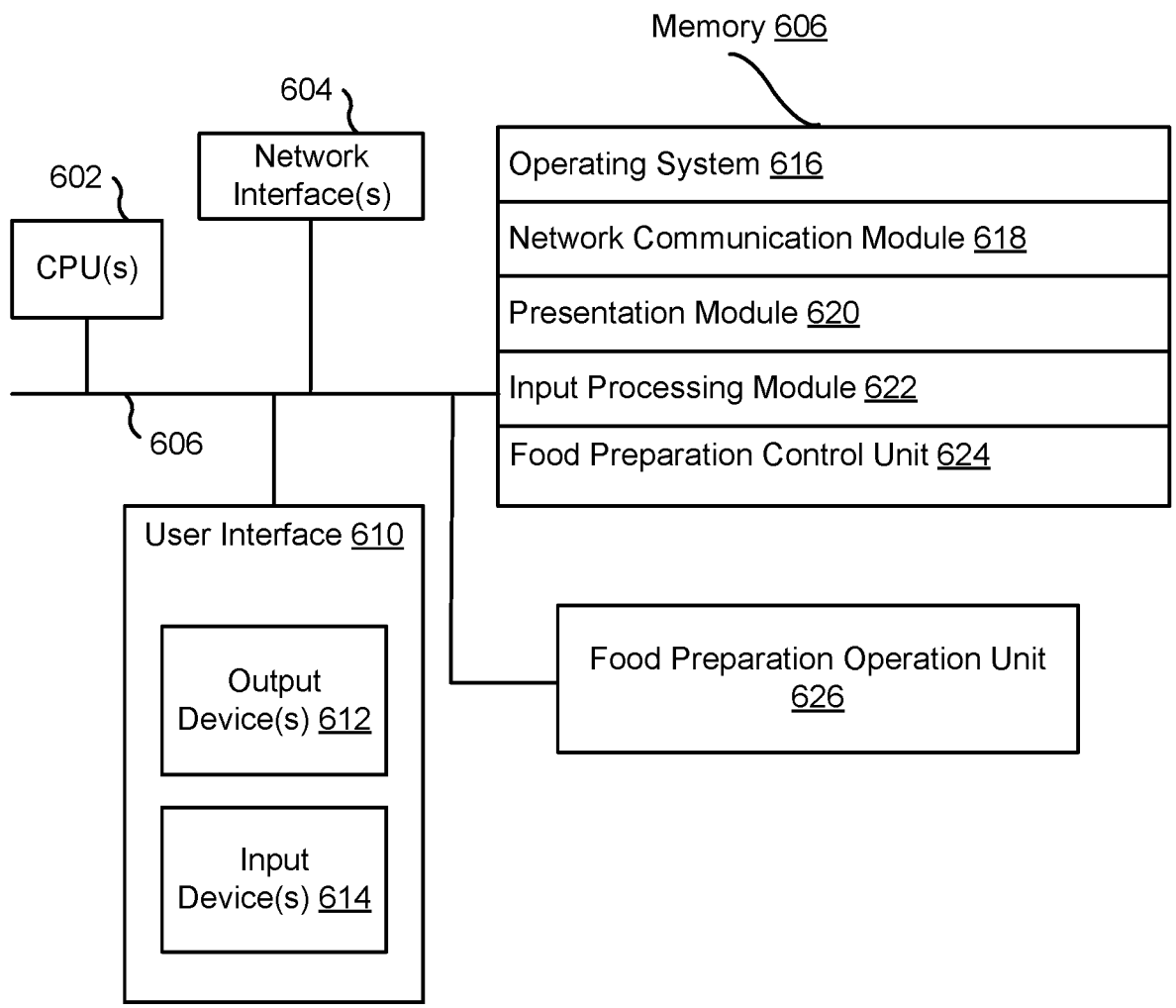
FIG. 6 is a block diagram of a cooking appliance in accordance with some embodiments.

FIG. 6 is a block diagram of an exemplary cooking appliance 600 in accordance with some embodiments. The cooking appliance 600 can serve as appliance 110, 112, 114, 140, 140', 200, 201, 202, 203, 204, for example, in various embodiments. The cooking appliance 800 includes one or more processing units (CPUs) 602, one or more network interfaces 604, memory 606, and one or more communication buses 608 for interconnecting these components (sometimes called a chipset). Cooking appliance 600 also includes a user interface 610. User interface 610 includes one or more output devices 612 that enable presentation of media content, including one or more speakers and/or one or more visual displays. User interface 610 also includes one or more input devices 614, including user interface components that facilitate user input such as a keyboard, a mouse, a voice-command input unit or microphone, a touch screen display, a touch-sensitive input pad, a gesture capturing camera, or other input buttons or controls. In some embodiments, cooking appliance 600 further includes sensors (e.g., sensors 141, 142 of FIG. 1B), which senses operating environment information of the cooking appliance 600. Sensors include but are not limited to one or more heat sensors, light sensors, one or more cameras, humidity sensors, one or more motion sensors, one or more biological sensors (e.g., a galvanic skin resistance sensor, a pulse oximeter, and the like), weight sensors, spectrometers, and other sensors. Furthermore, the cooking appliance 600 includes food preparation operation unit 626 (e.g., heating means that are based on electricity, induction, gas, radiation, etc.). Memory 606 includes non-volatile memory, such as one or more magnetic disk storage devices, one or more optical disk storage devices, one or more flash memory devices, or one or more other non-volatile solid state storage devices. Memory 606, optionally, includes one or more storage devices remotely located from one or more processing units 602. Memory 606, or alternatively the non-volatile memory within memory 606, includes a non-transitory computer readable storage medium. In some implementations, memory 606, or the non-transitory computer readable storage medium of memory 606, stores the following programs, modules, and data structures, or a subset or superset thereof:

- operating system 616 including procedures for handling various basic system services and for performing hardware dependent tasks;
- network communication module 618 for connecting to external services via one or more network interfaces 604 (wired or wireless);
- presentation module 620 for enabling presentation of information;
- input processing module 622 for detecting one or more user inputs or interactions from one of the one or more input devices 614 and interpreting the detected input or interaction;
- food preparation control unit 624, which controls the cooking appliance 600, including but not limited to modules of appliance 140 or 140' as forth herein.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various implementations. In some implementations, memory 606, optionally, stores a subset of the modules and data structures identified above. Furthermore, memory 606, optionally, stores additional modules and data structures not described above.

While particular embodiments are described above, it will be understood it is not intended to limit the application to these particular embodiments. On the contrary, the application includes alternatives, modifications and equivalents that are within the spirit and scope of the appended claims. Numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the embodiments.

Each of the above-identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various implementations. In some implementations, memory 606, optionally, stores a subset of the modules and data structures identified above. Furthermore, memory 806, optionally, stores additional modules and data structures not described above.

While particular embodiments are described above, it will be understood it is not intended to limit the application to these particular embodiments. On the contrary, the application includes alternatives, modifications and equivalents that are within the spirit and scope of the appended claims. Numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the embodiments.

What is claimed is:

1. A method, comprising:
at a device having one or more processors and memory:
receiving a user selection of a recipe from a plurality of recipes included in an interactive recipe program, wherein the recipe includes a sequence of ordered preparation steps and each preparation step corresponds to a respective sets of content items;
in response to receiving the user selection of the recipe, playing a first content item corresponding to a first preparation step of the selected recipe on a display, wherein the first content item is being played in a first media format;
while playing the first content item:
monitoring user's actions performing the first preparation step of the selected recipe; and
controlling one or more cooking appliances based on a first set of control instructions associated with the first preparation step;
in accordance with a determination that the user's actions performing the first preparation step meets a first criteria, adjusting the playing of the first content item, including displaying the first content item in a second media format, wherein the second media format differs from the first media format in at least a size and resolution of a portion of the first content item,
while displaying the first content item, in accordance with a determination that the user's actions are indicative of a question on the first preparation step:
searching a database associated with the first preparation step to retrieve one or more corresponding answers; and
displaying the retrieved one or more answers on the display concurrently with the first content item, and
while playing the first content item, determining that one or more conditions for playing the first content item in a third format are satisfied; and
in response to determining that the one or more conditions for playing the first content item in the third format are satisfied, playing the first content in the third format, wherein the first format is a video format, and the third format is an audio-only format, and wherein the one or more conditions include determining that the user is not looking at the display.

2. The method of claim 1, wherein adjusting the playing of the first content item includes pausing, replaying, or fast-forwarding in the first content item.

3. The method of claim 1, including:
while playing the first content item, detecting, using one or more user action monitoring devices, a current action performed by the user;
comparing the detected current action performed by the user with an action threshold of the preparation step;
providing, on the display, a warning to the user if the comparison determines that the current action does not fall within the action threshold; and
suggesting, on the display, to the user a course of correction on the display.

4. A device, comprising:
one or more processors; and
memory storing instructions, the instructions, when executed by the one or more processors, cause the processors to perform operations comprising:
receiving a user selection of a recipe from a plurality of recipes included in an interactive recipe program, wherein the recipe includes a sequence of ordered preparation steps and each preparation step corresponds to a respective set of content items;
in response to receiving the user selection of the recipe, playing a first content item corresponding to a first preparation step of the selected recipe on a display, wherein the first content item is being played in a first media format;
while playing the first content item:
monitoring the user's actions performing the first preparation step of the selected recipe; and
controlling one or more cooking appliances based on a first set of control instructions associated with the first preparation step;
in accordance with a determination that the user's actions performing the first preparation step meets a first criteria, adjusting the playing of the first content item, including displaying the first content item in a second media format, wherein the second media format differs from the first media format in at least a size and resolution of a portion of the first content item, and
while displaying the first content item, in accordance with a determination that the user's actions are indicative of a question on the first preparation step:
searching a database associated with the first preparation step to retrieve one or more corresponding answers;
displaying the retrieved one or more answers on the display concurrently with the first content item, and
while playing the first content item, determining that one or more conditions for playing the first content item in a third format are satisfied; and
in response to determining that the one or more conditions for playing the first content item in the third format are satisfied, playing the first content in the third format, wherein the first format is a video format, and the third format is an audio-only format, and wherein the one or more conditions include determining that the user is not looking at the display.

5. The device of claim 4, wherein adjusting the playing of the first content item includes pausing, replaying, or fast-forwarding in the first content item.

6. The device of claim 4, wherein the operations include:
while playing the first content item, detecting, using one or more user action monitoring devices, a current action performed by the user;
comparing the detected current action performed by the user with an action threshold of the preparation step;
providing, on the display, a warning to the user if the comparison determines that the current action does not fall within the action threshold; and
suggesting, on the display, to the user a course of correction on the display.

7. A non-transitory computer-readable storage medium storing instructions, the instructions, when executed by one or more processors, cause the processors to perform operations comprising:
receiving a user selection of a recipe from a plurality of recipes included in an interactive recipe program, wherein the recipe includes a sequence of ordered preparation steps and each preparation step corresponds to a respective set of content items;
in response to receiving the user selection of the recipe, playing a first content item corresponding to a first preparation step of the selected recipe on a display, wherein the first content item is being played in a first media format;
while playing the first content item:
monitoring the user's actions performing the first preparation step of the selected recipe; and
controlling one or more cooking appliances based on a first set of control instructions associated with the first preparation step;
in accordance with a determination that the user's actions performing the first preparation step meets a first criteria, adjusting the playing of the first content item, including displaying the first content item in a second media format, wherein the second media format differs from the first media format in at least a size and resolution of a portion of the first content item, and
while displaying the first content item, in accordance with a determination that the user's actions are indicative of a question on the first preparation step:
searching a database associated with the first preparation step to retrieve one or more corresponding answers;
displaying the retrieved one or more answers on the display concurrently with the first content item, and
while playing the first content item, determining that one or more conditions for playing the first content item in a third format are satisfied; and
in response to determining that the one or more conditions for playing the first content item in the third format are satisfied, playing the first content in the third format, wherein the first format is a video format, and the third format is an audio-only format, and wherein the one or more conditions include determining that the user is not looking at the display.

8. The non-transitory computer-readable storage medium of claim 7, wherein adjusting the playing of the first content item includes pausing, replaying, or fast-forwarding in the first content item.

* * * * *